United States Patent
Yoon

(10) Patent No.: US 10,584,067 B2
(45) Date of Patent: Mar. 10, 2020

(54) HIGH INTENSITY FOCUSED ULTRASONIC PIEZOELECTRIC ACTUATOR AND METHOD OF MANUFACTURING THE SAME

(71) Applicant: ECO DM LAB Co., Ltd., Cheongju-Si (KR)

(72) Inventor: Mansoon Yoon, Cheongju-Si (KR)

(73) Assignee: ECO DM LAB CO., LTD., Cheongju-si, Chungcheongbuk-Do (KR)

( * ) Notice: Subject to any disclaimer, the term of this patent is extended or adjusted under 35 U.S.C. 154(b) by 1051 days.

(21) Appl. No.: 14/884,089

(22) Filed: Oct. 15, 2015

(65) Prior Publication Data

US 2016/0184613 A1    Jun. 30, 2016

(51) Int. Cl.

| | | |
|---|---|---|
| C04B 35/491 | (2006.01) | |
| C04B 35/638 | (2006.01) | |
| B28B 1/24 | (2006.01) | |
| H01L 41/333 | (2013.01) | |
| A61N 7/02 | (2006.01) | |
| C04B 35/472 | (2006.01) | |
| C04B 35/64 | (2006.01) | |
| C04B 35/626 | (2006.01) | |
| B06B 1/06 | (2006.01) | |

(52) U.S. Cl.
CPC .......... *C04B 35/472* (2013.01); *B06B 1/0651* (2013.01); *B28B 1/24* (2013.01); *C04B 35/491* (2013.01); *C04B 35/62695* (2013.01); *C04B 35/638* (2013.01); *C04B 35/64* (2013.01); *H01L 41/333* (2013.01); *A61N 7/02* (2013.01); *C04B 2235/3248* (2013.01); *C04B 2235/528* (2013.01); *C04B 2235/5445* (2013.01); *C04B 2235/6022* (2013.01); *C04B 2235/94* (2013.01)

(58) Field of Classification Search
CPC .. H01L 41/1876; H01L 41/047; H01L 41/098

USPC ................ 310/334, 332, 369, 337
See application file for complete search history.

(56) References Cited

U.S. PATENT DOCUMENTS

| | | | |
|---|---|---|---|
| 7,567,017 B2 * | 7/2009 | Yoon | H02N 2/025 |
| | | | 310/328 |
| 8,382,280 B2 * | 2/2013 | Gupta | G02B 3/14 |
| | | | 351/159.11 |
| 2009/0171251 A1 * | 7/2009 | Rybyanets | A61H 9/0057 |
| | | | 601/2 |

FOREIGN PATENT DOCUMENTS

KR    20030095638 A    12/2003

\* cited by examiner

*Primary Examiner* — Thomas M Dougherty
*Assistant Examiner* — Karen B Addison
(74) *Attorney, Agent, or Firm* — Ferguson Braswell Frsaer Kubasta PC

(57) ABSTRACT

Disclosed is a focused ultrasonic piezoelectric actuator having a novel type of piezoelectric device for focusing ultrasonic waves. The focused ultrasonic piezoelectric actuator includes a dome-shaped piezoelectric body for focusing ultrasonic waves and a rim configured to facilitate focusing of ultrasonic waves of the body and injection of the dome-shaped piezoelectric body during a powder injection molding process, remove warpage of the dome-shaped body during a sintering process, and reinforce focusing intensity of the ultrasonic waves. The rim is integrally formed with the body. Accordingly, in the focused ultrasonic piezoelectric actuator, a dome-shaped focused ultrasonic piezoelectric actuator for focusing ultrasonic waves using a thickness vibration mode at a MHz frequency band is easily manufactured by a powder injection molding method, and thus an ultrasonic focusing effect is maximized.

4 Claims, 10 Drawing Sheets

PRIOR ART

PRIOR ART

HIGH INTENSITY FOCUSED ULTRASONIC PIEZOELECTRIC ACTUATOR AND METHOD OF MANUFACTURING THE SAME

CROSS-REFERENCE TO RELATED APPLICATION

This application claims priority to and the benefit of Korean Patent Application No. 2014-0194202, filed on Dec. 30, 2014, the disclosure of which is incorporated herein by reference in its entirety.

BACKGROUND

1. Field of the Invention

The present invention relates to a focused ultrasonic piezoelectric actuator and a method of manufacturing the same. More specifically, the present invention relates to a focused ultrasonic piezoelectric actuator for focusing ultrasonic waves using a thickness vibration mode at a MHz frequency band, and a method of manufacturing the same. The focused ultrasonic piezoelectric actuator is easily fabricated by a powder injection molding method and capable of maximizing an ultrasonic focusing efficiency.

2. Discussion of Related Art

Normally, focused ultrasonic piezoelectric actuators used in medical devices are based on optical principles. Since the focused ultrasonic piezoelectric actuator is manufactured by processing a piezoelectric device to have a spherical lens shape, it can focus ultrasonic energy generated by voltage application in a thickness vibration mode into a focal point of curvature, and thereby concentrate the ultrasonic energy. Accordingly, the focused ultrasonic piezoelectric actuator has been used in a surgical procedure for burning away malignant tumor in a human body or burning and decomposing fat and, recently, widely used for the purpose of regeneration of skin by irradiating facial skin with the ultrasonic energy generated from the focused ultrasonic piezoelectric actuator.

Piezoelectric ceramics are materials that convert electric energy into mechanical energy. When piezoelectric ceramics having predetermined thicknesses are resonated in thickness directions, resonant frequencies vary according to the thicknesses to be the same as an applied frequency, and thereby ultrasonic waves are generated. Here, an optical principle may be applied to focus the generated ultrasonic vibration.

FIG. 1 is a view for describing a principle of focusing light in a spherical lens.

As illustrated in FIG. 1, light passing through a spherical lens 5 have different focal lengths according to wavelengths of the light. That is, as the wavelength of the light increases, a focal length of the light decreases. Since the piezoelectric ceramics have maximum displacement values at resonant frequencies thereof, the piezoelectric ceramics are normally operated at the resonant frequencies when used as ultrasonic devices.

FIG. 2 is a view illustrating a direction of vibration displacement generated when a disk-type piezoelectric vibrator is operated in a thickness vibration mode.

As illustrated in FIG. 2, the disk-type piezoelectric vibrator 10 has a maximum displacement in a thickness direction at a resonance frequency thereof since it uses thickness vibration. A piezoelectric material has its own frequency integer, and the frequency integer is represented by the following Formula 1.

$$N_t = f_r \times t [H_z \cdot m] \quad \text{[Formula 1]}$$

$N_t$: frequency integer
$f_r$: first resonant frequency [Hz]
t: thickness of specimen [meter]

A resonant frequency according to a thickness of a specimen is determined by Formula 1. For example, when the frequency integer is 2100, a thickness of a piezoelectric material having a resonant frequency of 2 MHz in a thickness direction may be determined as follows.

$$t \text{ [m]} = N_t/f_r = 2100/(2 \times 10^6) = 1.05 \times 10^{-3} \text{ [m]} = 1.05 \text{ [mm]}$$

That is, in order to manufacture an ultrasonic vibrator having the resonant frequency of 2 MHz in a thickness direction, the piezoelectric material needs to be fabricated to have a thickness of 1.05 mm. A piezoelectric device having a preferred resonant frequency may be manufactured according to a frequency integer of a piezoelectric material.

Accordingly, a piezoelectric device may be designed to have a preferred focal length by using a principle of a spherical lens and a frequency integer in a thickness vibration mode. That is, a focused ultrasonic device having a preferred frequency and focal length may be fabricated by manufacturing a piezoelectric device to have a thickness of the preferred frequency for generating ultrasonic waves and to have a hemispherical shape. Normally, ultrasonic waves are focused in an area corresponding to a radius of curvature of a dome-shaped piezoelectric device.

FIG. 3(a) is a view illustrating a bulk-type piezoelectric device, and FIG. 3(b) is a view illustrating a state in which the bulk-type piezoelectric device of FIG. 3(a) is processed to have a preferred thickness.

Conventionally, a bulk-type piezoelectric device 10 as illustrated in FIG. 3(a) is manufactured, and then the bulk-type piezoelectric device 10 is processed to have a preferred thickness and radius of curvature as illustrated in FIG. 3(b) by using a grinding machine as a lens-processing method.

Accordingly, a large amount of the materials may be consumed and cracks may easily occur since the piezoelectric ceramics are brittle during processing, resulting in rise of manufacturing costs in a mass production process.

Normally, dome-shaped piezoelectric ultrasonic devices used for skin regeneration mainly have a resonant frequency of 4 MHz or 7 MHz. According to Formula 1, the dome-shaped piezoelectric ultrasonic devices are subjected to rounding processing to have thicknesses of 0.525 mm and 0.3 mm, respectively. Thus, as the resonant frequency increases, the thickness of the dome-shaped piezoelectric ultrasonic device is reduced to 0.3 mm or less. Accordingly, internal stress caused by the processing of a brittle piezoelectric material is increasingly accumulated and risk of breakage increases while the dome-shaped piezoelectric ultrasonic device vibrates by a strong AC electric field of 250 $V_{rms}$/mm.

In addition to such problems due to mechanical processing, spurious vibrations generated in edge portions of the conventional dome-shaped focused ultrasonic device may prevent focusing of ultrasonic waves and thereby reduce an ultrasonic focusing efficiency.

As a reference, a piezoelectric-piezoelectric ceramic actuator having opposite polarization directions is disclosed in Korea Publication Patent No. 10-2003-0095638 (published on Dec. 24, 2003).

SUMMARY OF THE INVENTION

The present invention is directed to a dome-shaped focused ultrasonic device manufactured by a powder injection molding technique. The technique allows excellent mass productivity and high dimensional accuracy and is easy to manufacture any shape of structures. At the same time, the present invention is directed to a focused ultrasonic piezoelectric actuator in which mass productivity is maximized and breakage of the piezoelectric material and internal stress occurring due to mechanical processing is fundamentally suppressed, and which takes full advantage of an ultrasonic focusing effect by removing spurious vibrations, and a method of manufacturing the same.

According to an aspect of the present invention, there is provided a focused ultrasonic piezoelectric actuator including a dome-shaped body, and a rim formed to extend integrally from an edge of the body and protrude from the edge of the body.

According to another aspect of the present invention, there is provided a method of manufacturing a focused ultrasonic piezoelectric actuator including (a) mixing a PZT powder and a binder with a solvent, cooling the mixture, and pulverizing the mixture to form pellets for injection molding, (b) inputting the pulverized pellets into an injection mold, and melting and injection-molding the pellets to form an injection molded article, and (c) firstly removing the binder from the injection molded article by a solvent extraction method, secondly removing the binder from the injection molded article by a pyrolysis method, and sintering the injection molded article to form a piezoelectric actuator having a dome-shaped body and a rim extending to protrude from the body.

BRIEF DESCRIPTION OF THE DRAWINGS

The above and other objects, features, and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Embodiments of the present invention will be described in detail below with reference to the accompanying drawings. While the present invention is shown and described in connection with the embodiments thereof, it will be apparent to those skilled in the art that various modifications can be made without departing from the spirit and scope of the present invention. Accordingly, the scope of the present invention should be determined by the appended claims. Like numerals refer to like elements throughout the specification.

Hereinafter, a focused ultrasonic piezoelectric actuator according to an embodiment of the present invention and a method of manufacturing the same will be described in detail with reference to the accompanying drawings.

FIGS. 4(a) and 4(b) are views illustrating results of a simulation, which show a resonant frequency and ultrasonic vibrations of a dome-shaped rimless focused ultrasonic piezoelectric actuator in a thickness vibration mode. Here, a material for the simulation is P8-1 in a hard PZT group, which is used as an ultrasonic vibrator. In addition, the dome has a thickness of 0.5 mm, a diameter of 15 mm, and a height of 3.2 mm.

As illustrated in FIG. 4(a), when the thickness of the dome is 0.5 mm, the resonant frequency obtained from the simulation is 4.4 MHz in the thickness vibration mode. FIG. 4(b) shows directions of thickness vibration displacement, which are obtained by applying an alternating current (AC) electric field at the frequency of 4.4 MHz.

As illustrated in FIG. 4(b), spurious vibrations that are not focused within a radius of curvature of the dome exist in an edge E of the piezoelectric actuator. However, ultrasonic vibrations in a center portion M of the piezoelectric actuator are focused. Such spurious vibrations that are not destined to a center of the radius of curvature of the dome may weaken ultrasonic focusing intensity. Thus, this type of dome shape may be inefficient for focusing ultrasonic waves.

A focused ultrasonic piezoelectric actuator according to an embodiment of the present invention has a structure capable of preventing the ultrasonic focusing intensity from being weaken due to the spurious vibrations. Hereinafter, this will be described in more detail with reference to the accompanying drawings.

Figure 5:
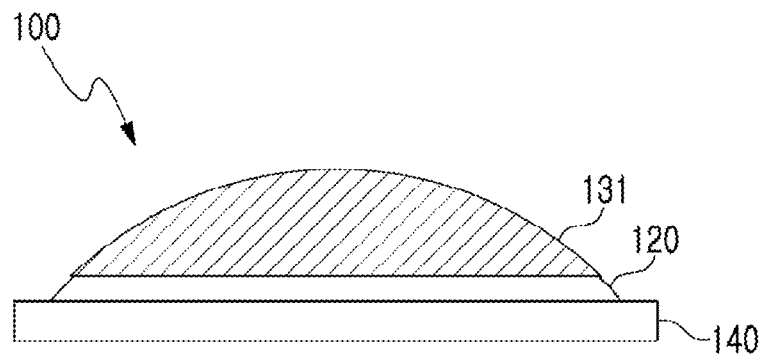
FIGS. 5(a) and 5(b) are respectively a front view and a perspective view illustrating a focused ultrasonic piezoelectric actuator according to an embodiment of the present invention.
Figure 5:
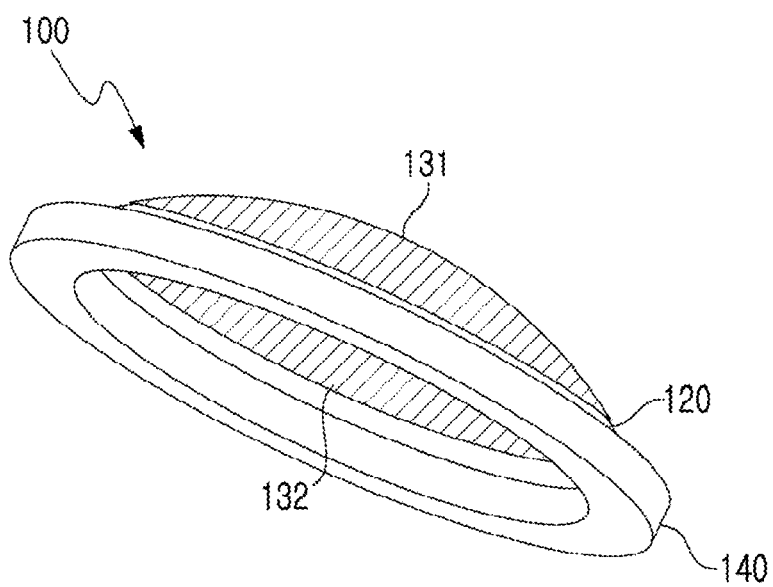

FIGS. 5(a) and 5(b) are respectively a front view and a perspective view illustrating a focused ultrasonic piezoelectric actuator according to an embodiment of the present invention.

As illustrated in FIGS. 5(a) and 5(b), the focused ultrasonic piezoelectric actuator 100 according to the embodiment of the present invention includes a dome-shaped body 120 and a rim 140 formed to extend integrally from an edge of the body 120 and protrude from the edge of the body 120.

Here, the entire body 120 may preferably have the same thickness. In addition, the rim 140 is formed of the same piezoelectric material as the body 120 and serves to suppress spurious vibrations. A thickness of the rim 140 may be preferably an even multiple of the thickness of the body.

As shown in FIGS. 5(a) and 5(b), the focused ultrasonic piezoelectric actuator 100 according to an embodiment of the present invention may further include first electrode 131 and second electrodes 132 respectively formed on both sides of the body 120. Here, the first electrode 131 and the second electrode 132 may not be formed on the rim 140. The first electrode 131 and the second electrode 132 may be formed by coating upper and lower surfaces of the body 120 with a silver paste and curing the silver paste.

Figure 6:
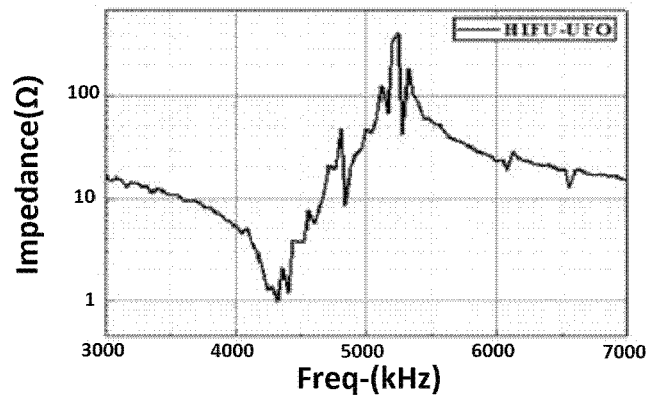
FIGS. 6(a), 6(b), and 6(c) are views illustrating results of a simulation, which show a resonant frequency and ultrasonic vibrations of a dome-shaped focused ultrasonic piezoelectric actuator according to an embodiment of the present invention in a thickness vibration mode.
Figure 6:
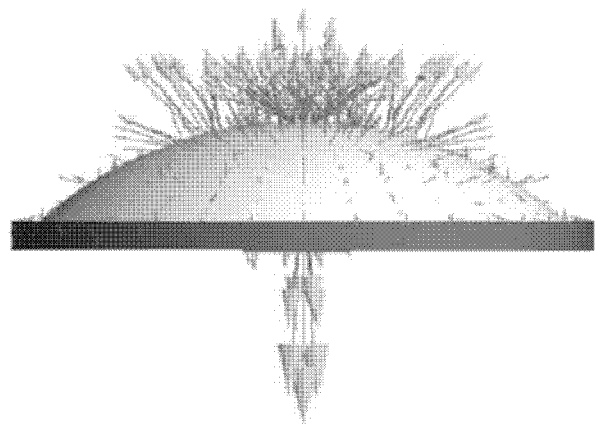
Figure 6:
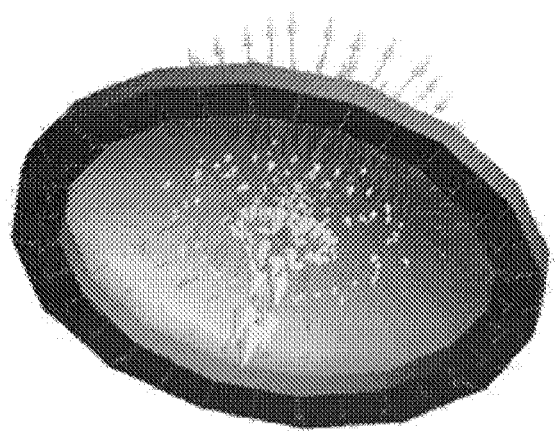

FIGS. 6(*a*), 6(*b*), and 6(*c*) are views illustrating results of a simulation, which show a resonant frequency and ultrasonic vibrations of a dome-shaped focused ultrasonic piezoelectric actuator according to an embodiment of the present invention in a thickness vibration mode. Here, a material for the simulation is P8-1 in a hard PZT group, which is used as an ultrasonic vibrator. In addition, the dome has a thickness of 0.5 mm, a diameter of 15 mm, and a height of 3.2 mm. Further, the rim is designed to have a diameter of 16.6 mm and a thickness of 1 mm.

An important thing to be considered for determining the thickness of the rim is that the thickness of the rim is designed to be an even multiple of the thickness of the dome so that spurious vibrations generated in an edge of the dome during a thickness vibration mode are suppressed by the rim. This may be represented by the following Formula 2.

$$t = (n \times \lambda)/2 \qquad \text{[Formula 2]}$$

t: thickness of dome or rim
n: integer
λ: wavelength

Here, the maximum vibration, that is, a resonance, occurs when n is an odd number, and an anti-resonance state at which the vibration displacement is minimized comes when n is an even number. Accordingly, if the maximum displacement in a thickness direction occurs at about 4 MHz when the thickness of the dome is 0.5 mm, the anti-resonance state (the minimum vibration displacement) comes when the thickness of the dome is 1 mm. Accordingly, when the thickness of the dome is 0.5 mm and the thickness of the rim is 1 mm, vibrations in a thickness direction hardly occur in the rim in the thickness vibration mode at about 4 MHz.

Here, the thickness of the dome used in the simulation according to the embodiment of the present invention is 0.5 mm. As a result of the simulation, a resonant frequency in the thickness vibration mode is 4.24 MHz. FIGS. 6(*b*) and 6(*c*) illustrate directions of the thickness vibration displacement generated by applying an AC electric field at a frequency of 4.24 MHz.

Figure 1:
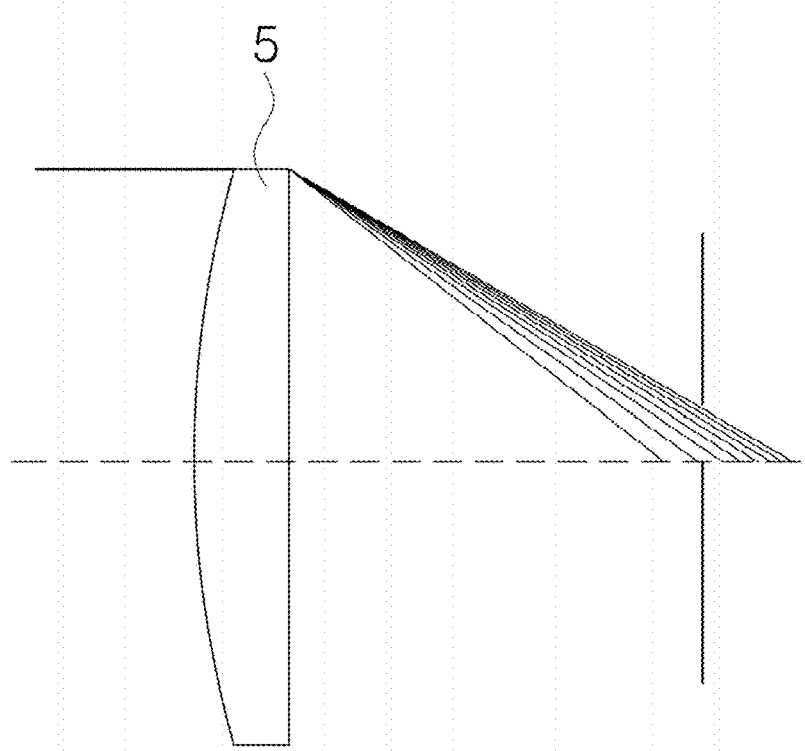
FIG. 1 is a view for describing a principle of focusing light in a spherical lens.
Figure 2:
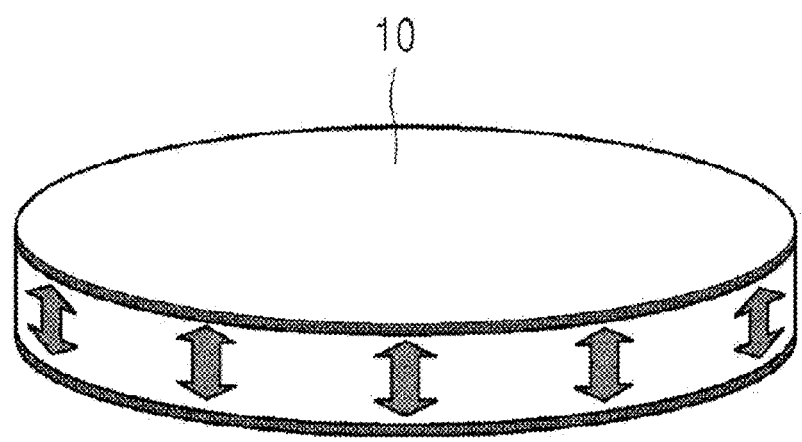
FIG. 2 is a view illustrating a direction of vibration displacement generated when a disk-type piezoelectric vibrator is operated in a thickness vibration mode.
Figure 3:
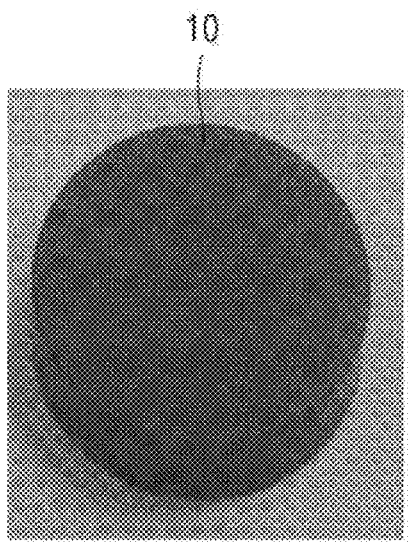
FIG. 3(a) is a view illustrating a bulk-type piezoelectric device.
FIG. 3(b) is a view illustrating a state in which the bulk-type piezoelectric device of FIG. 3(a) is processed to have a preferred thickness.
Figure 3:
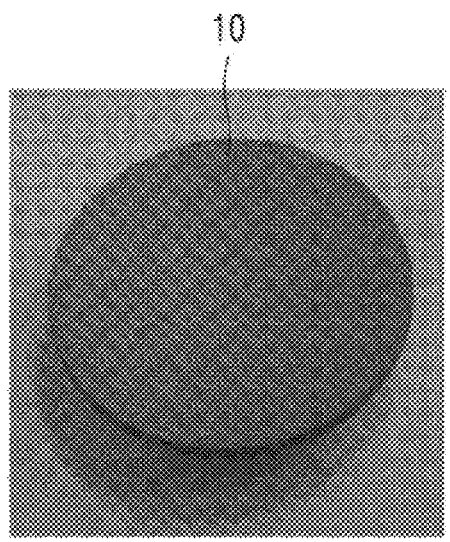
Figure 4:
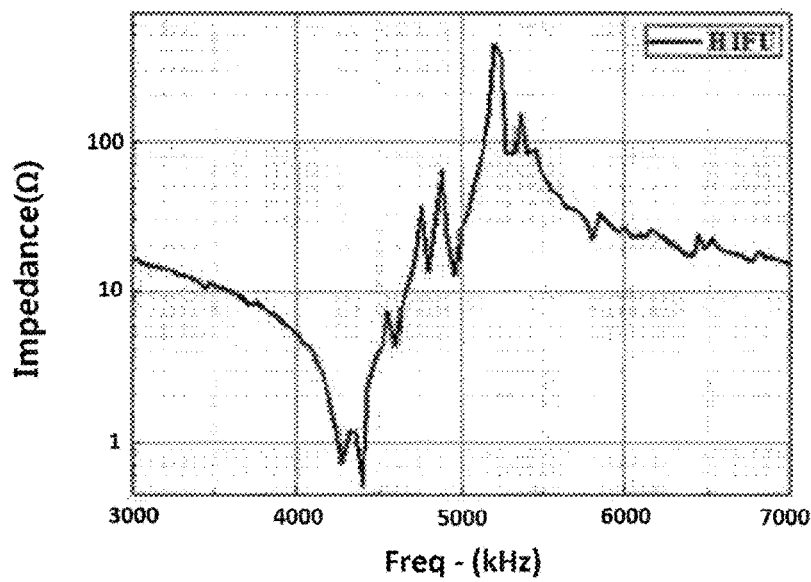
FIGS. 4(a) and 4(b) are views illustrating results of a simulation, which show a resonant frequency and ultrasonic vibrations of a rimless dome-shaped focused ultrasonic piezoelectric actuator in a thickness vibration mode.
Figure 4:
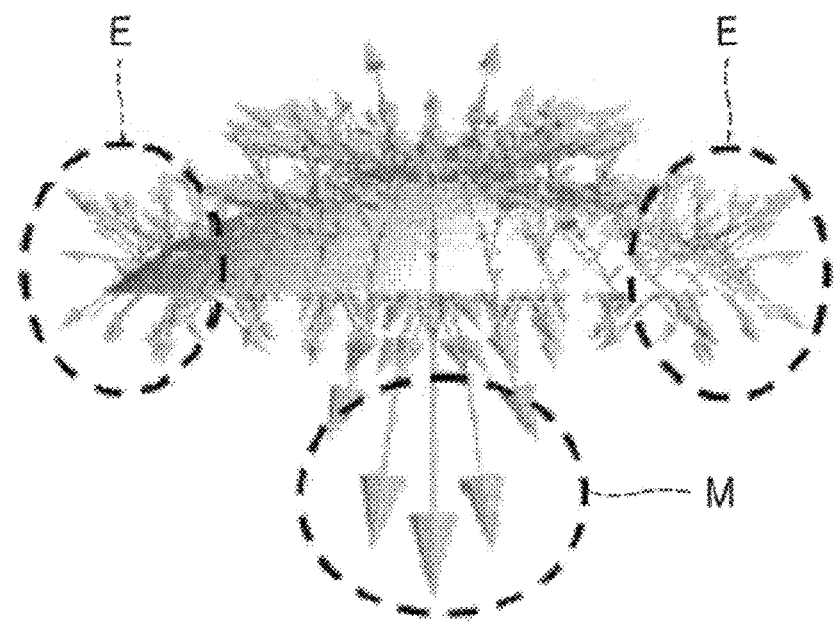

Referring to FIGS. 6(*b*) and 6(*c*), spurious vibrations, which are generated in an edge of the dome and not focused within the radius of curvature of the dome as illustrated in FIG. 4(*b*), are suppressed and disappeared by the rim, and ultrasonic waves are uniformly focused on a center portion of the dome.

Accordingly, by designing and manufacturing a rim in a dome-shaped focused ultrasonic piezoelectric actuator according to the design criteria described in Formula 2, spurious vibrations that are not destined to the center of the radius of curvature and weaken a focusing intensity of the ultrasonic waves may be effectively removed.

As described above, the dome-shaped focused ultrasonic piezoelectric actuator including the rim plays a significant role in a manufacturing process as well as it functionally has an excellent focusing efficiency compared to a rimless piezoelectric actuator.

This will be described in a powder injection molding process, which is used to manufacture the dome-shaped focused ultrasonic piezoelectric actuator including the rim according to the embodiment of the present invention, hereinafter.

Figure 7:
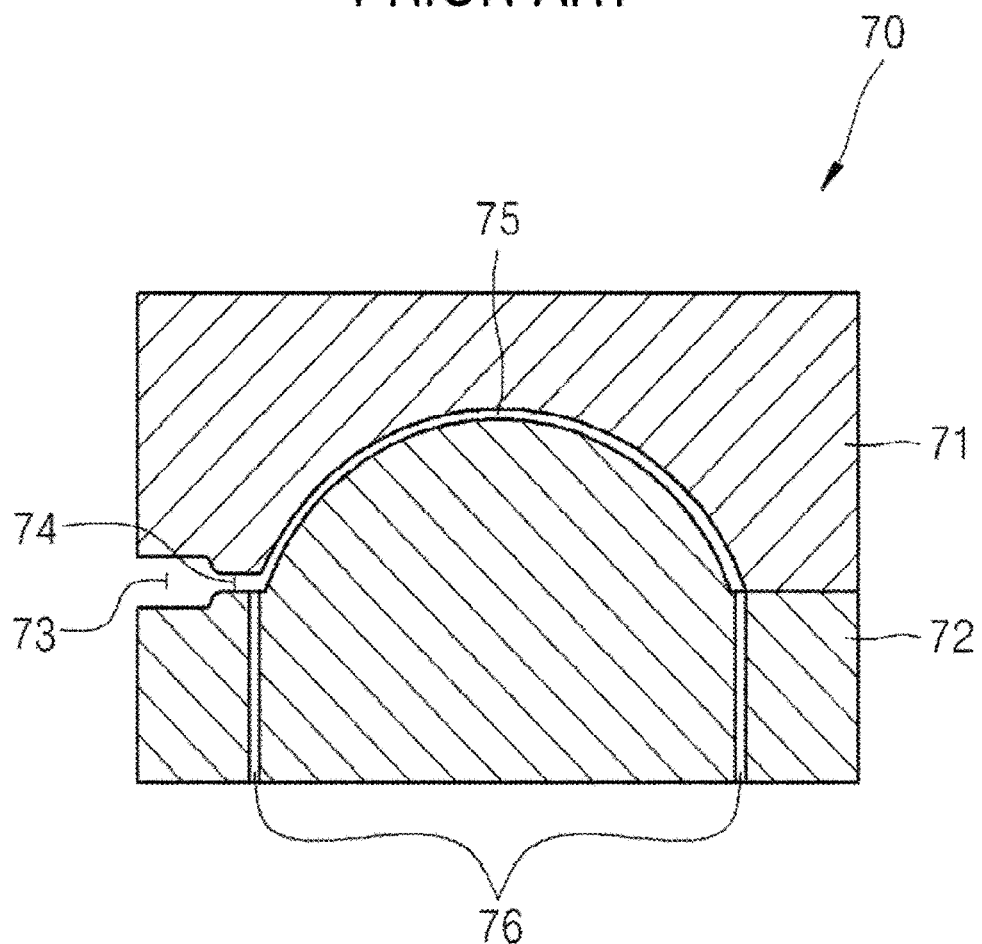
FIG. 7 is a view illustrating an injection mold for manufacturing a rimless focused ultrasonic piezoelectric actuator.
Figure 8:
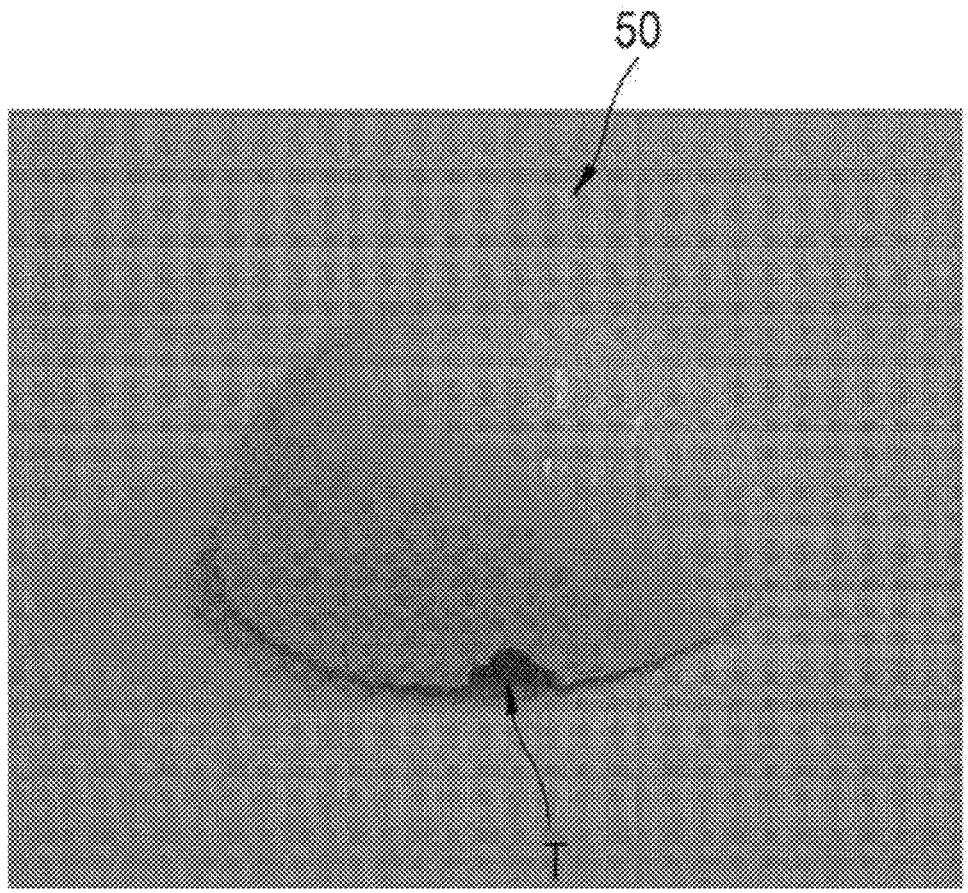
FIG. 8 is a photograph of a piezoelectric actuator manufactured using the injection mold of FIG. 7.

FIG. 7 is a view illustrating an injection mold for manufacturing a rimless focused ultrasonic piezoelectric actuator, and FIG. 8 is a photograph illustrating a piezoelectric actuator manufactured by the injection mold of FIG. 7.

As illustrated in FIGS. 7 and 8, a rimless dome-shaped piezoelectric actuator is manufactured in a molding machine having the same structure as a normal plastic injection molding machine.

Here, an injection mold 70 for manufacturing the rimless focused ultrasonic piezoelectric actuator includes a fixed body 71 and a moving body 72. A product is molded in such a manner that when a cavity 75 is filled with a molding powder input into a runner 73 via a gate 74, the moving body 72 is separated from the fixed body 71 and the product is unmolded by an ejector pin 76.

Here, in the process of forming the cavity 75, since the runner 73 and the gate 74 are formed between the fixed body 71 and the moving body 72, a gate mark remains in a side portion of the product. In this case, since the gate mark remains after the injection molding process, it is seen near an edge portion. When the focused ultrasonic piezoelectric actuator has a small thickness, the edge portion T may be frequently broken during a process of removing the gate mark, which results in degradation of product yield. In addition, since a product having a resonant frequency of 7 MHz is very thin to have a thickness of about 0.3 mm, the ejector pin 76 is as sharp as a needle and thus may remain a defect or generate micro-cracks in a lower portion of the product.

Figure 9:
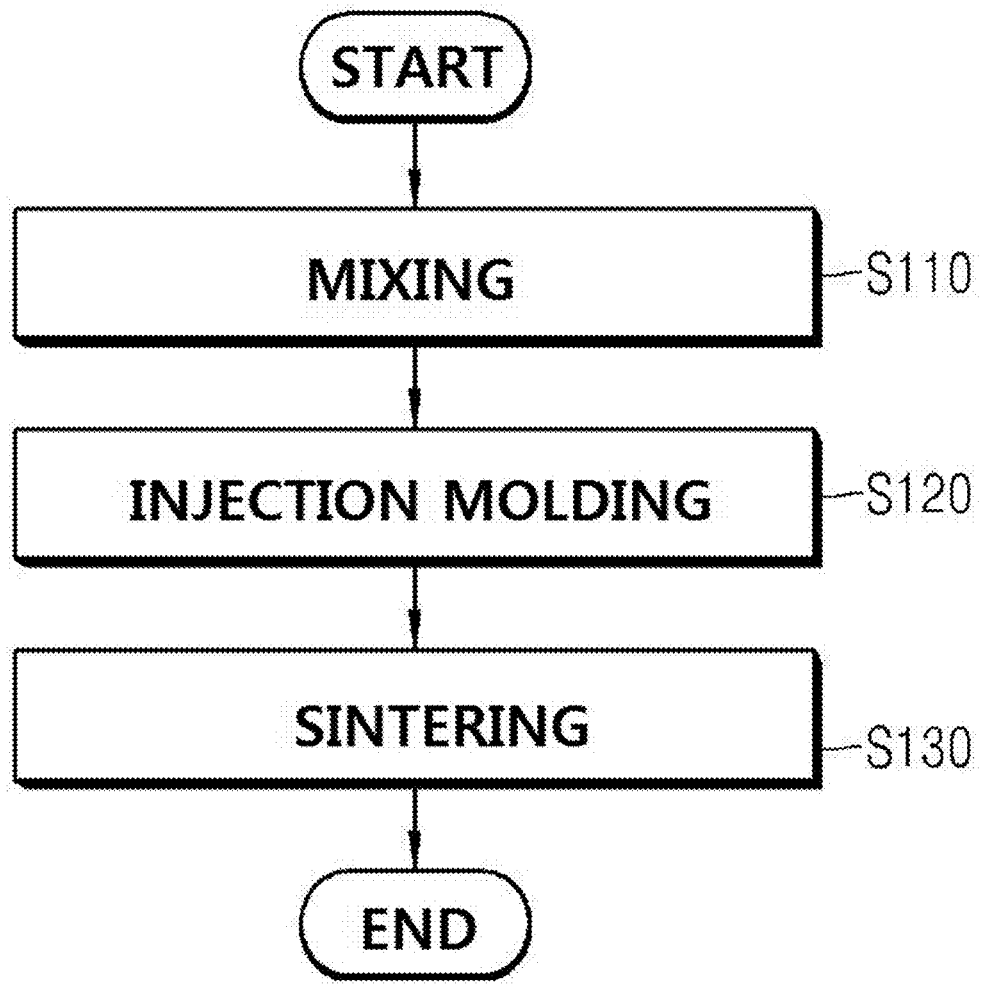
FIG. 9 is a process flowchart illustrating a method of manufacturing a focused ultrasonic piezoelectric actuator according to an embodiment of the present invention.
Figure 10:
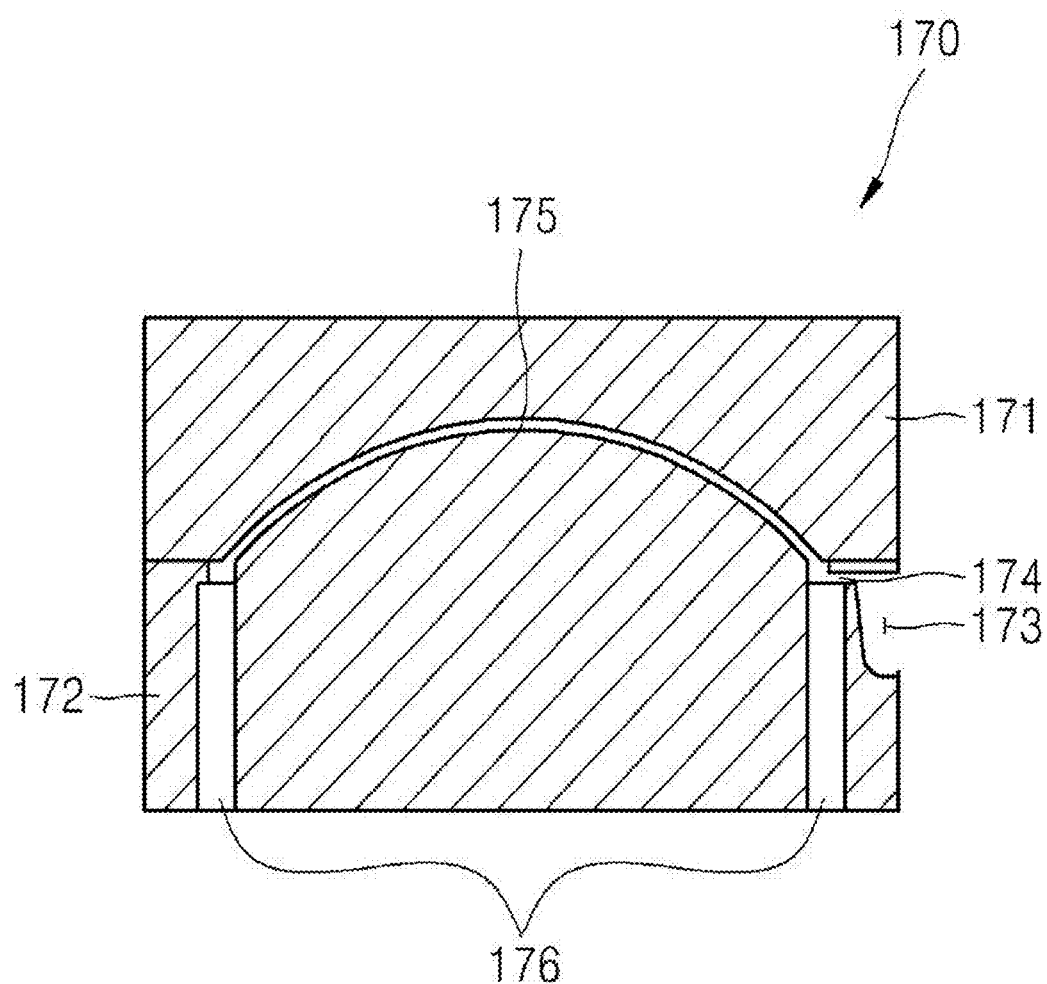
FIG. 10 is a view illustrating an injection mold for manufacturing a focused ultrasonic piezoelectric actuator according to an embodiment of the present invention.
Figure 11:
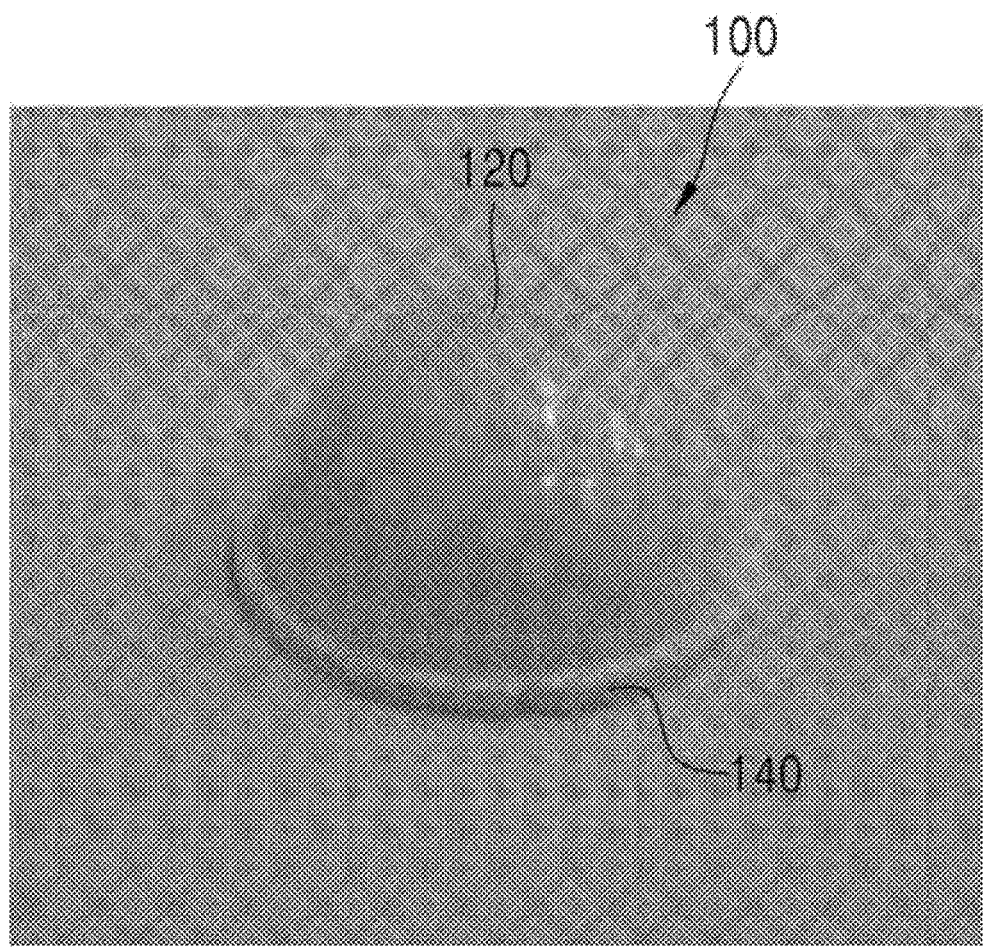
FIG. 11 is a photograph of a piezoelectric actuator manufactured using the injection mold of FIG. 10.

FIG. 9 is a process flowchart illustrating a method of manufacturing a focused ultrasonic piezoelectric actuator according to an embodiment of the present invention, FIG. 10 is a view illustrating an injection mold for manufacturing a focused ultrasonic piezoelectric actuator according to an embodiment of the present invention, and FIG. 11 is a photograph of a piezoelectric actuator manufactured using the injection mold of FIG. 10.

As illustrated in FIG. 9, the method of manufacturing the focused ultrasonic piezoelectric actuator according to the embodiment of the present invention includes a mixing process (S110), an injection molding process (S120), and a sintering process (S130).

Mixing

In the mixing process (S110), a PZT powder and a binder are mixed with a solvent, cooled, and pulverized into pellets for injection molding.

Here, the PZT powder includes $Pb(Zr,Ti)O_3$ as a main component. The PZT powder is calcinated, synthesized into a single-phased PZT powder, pulverized into particles having a thickness of 300 nm by a high-energy milling process, and dried to form a spherical powder by a spray dryer.

In addition, the binder consists of polybutyl methacrylate (PBMA) and paraffin wax (PA) in an appropriate ratio, and the rest is ethylene vinyl acetate (EVA) which is soluble in a petroleum-based solvent. The manufactured PZT powder and binder are measured to a volume ratio of 45% to 55%, mixed with the solvent for about one hour at a temperature of 150° C. in a pressurized kneader in which two Banbury-type blades rotate, cooled, and pulverized and granulated into the pellets for injection molding.

Injection Molding

In the injection molding process (S120), the pulverized pellets are input to the injection mold, melted, and injection-molded to form an injection molded article.

Here, as illustrated in FIG. 11, the focused ultrasonic piezoelectric actuator 100 consists of a dome-shaped body 120 in which thickness vibrations occur, and a rim 140 in which thickness vibrations is suppressed are integrally combined.

For this, as illustrated in FIGS. 10 and 11, an injection mold 170 for manufacturing a focused ultrasonic piezoelectric actuator 100 according to an embodiment of the present invention includes a fixed body 171 and a moving body 172. A product is molded in such a manner that when a cavity 175 is filled with a molding powder input into a runner 173 via a gate 174, the moving body 172 is separated from the fixed body 171 and the product is unmolded by an ejector pin 176.

Here, in the process of filling the cavity 175, since the runner 173 and the gate 174 are deposited at corresponding position to the rim formed integrally with the dome-shaped body 120, a gate mark remains on a side surface of the rim 140, which does not affect the dome-shaped body 120.

Accordingly, since the product is unmolded by the ejector pin 176 disposed below the rim 140 that is not related to ultrasonic vibrations and does not affect the shape of the dome-shaped body 120, the product yield may be maximized. In addition, since a thickness of the rim 140 is designed to be an even multiple of the thickness of the dome, the rim 140 may function to reinforce the strength of an injection molded article. Thus, a robust product may be manufactured even when the product is transferred or sintered.

Sintering

In the sintering process (S130), the binder is firstly removed from the injection molded article by a solvent extraction method, and secondly removed from the injection molded article by a pyrolysis method. Then, the injection molded article is sintered to form the piezoelectric actuator 100 including the dome-shaped body 120 and the rim 140 extending to protrude from the body 120.

Here, the binder may be preferably removed through a combination of the solvent extraction method and the pyrolysis method. The injection molded article in which the binder is removed may be sintered at a temperature of 1250±50° C. preferably in a closed aluminum crucible in order to prevent volatilization of PbO.

The focused ultrasonic piezoelectric actuator according to the embodiment of the present invention is manufactured by a powder injection molding technique according to the above-described processes (S110 to S130). Accordingly, compared to a normal method, internal stress due to processing may not occur regardless of a thickness of the product, and high manufacturing yield may be obtained since cracking phenomena occurring during processing is suppressed. In addition, since the rim is formed integrally with the dome-shaped body, limitation in thickness of the dome-shaped body in the manufacturing process may be compensated for, a focusing efficiency of ultrasonic waves may be maximized, and the accuracy and yield of the product may be significantly improved.

While embodiments of the present invention have been shown and described above, it will be apparent to those skilled in the art that modifications and variations could be made without departing from the scope of the present invention as defined by the appended claims. Accordingly, the scope of the invention should be determined by the appended claims.

What is claimed is:

1. A focused ultrasonic piezoelectric actuator comprising:
a dome-shaped body; and
a rim formed to extend integrally from an edge of the body and protrude from the edge of the body,
wherein the rim is formed of a same piezoelectric material as the body, and serves to suppress spurious vibrations.

2. The focused ultrasonic piezoelectric actuator of claim 1, wherein the entire body has the same thickness.

3. The focused ultrasonic piezoelectric actuator of claim 1, wherein a thickness of the rim is an even multiple of a thickness of the body.

4. The focused ultrasonic piezoelectric actuator of claim 1, further comprising a first electrode and a second electrode respectively formed on both sides of the body.

* * * * *